United States Patent [19]
Canfield

[11] Patent Number: 5,131,283
[45] Date of Patent: Jul. 21, 1992

[54] TOOL FOR SAMPLING OIL FROM ELECTRIC DISTRIBUTION TRANSFORMER TANKS FOR PCB CONTAMINATION

[76] Inventor: Michael H. Canfield, 406 Normandy Rd., Versailles, Ky. 40383

[21] Appl. No.: 618,063

[22] Filed: Nov. 26, 1990

[51] Int. Cl.$^5$ .............................................. G01N 1/14
[52] U.S. Cl. .............................. 73/864.74; 73/863.85; 137/318
[58] Field of Search ............. 73/863.85, 864.74, 864.34, 73/863.81; 137/318, 327, 328

[56] References Cited

U.S. PATENT DOCUMENTS

| | | | |
|---|---|---|---|
| 552,408 | 12/1895 | Barnes | 137/318 X |
| 3,201,994 | 8/1965 | Adams | 73/864.74 X |
| 3,206,982 | 9/1965 | Blondfield | 73/864.74 X |
| 3,412,613 | 11/1968 | Brown et al. | 73/864.74 X |
| 3,534,613 | 10/1970 | Travor et al. | 73/864.74 X |
| 3,915,192 | 10/1975 | Skvarenina | 137/318 |
| 4,010,648 | 3/1977 | Harris, Sr. et al. | 73/863.85 |
| 4,046,013 | 9/1977 | Green | 73/863.85 X |
| 4,056,981 | 11/1977 | Kalka et al. | 73/863.85 |
| 4,598,731 | 7/1986 | Colson | 137/318 |
| 4,809,735 | 3/1989 | Volstadt et al. | 137/318 |

*Primary Examiner*—Tom Noland
*Attorney, Agent, or Firm*—Maurice L. Miller, Jr.

[57] ABSTRACT

A tool for piercing an electric distribution transformer tank for obtaining a sample of oil therefrom to be tested for PCB contamination is disclosed. The tool includes a threaded body with a wrenchable fitting on one end and a tank punch pin on the other and is adapted for threadable insertion into a threaded hollow shaft of a ground lug nut attached to the tank. The pin is advanced in the lug nut shaft to pierce the tank by wrenchably rotating the fitting. Hollow shafts formed through the pin, punch body and fitting provide a path for the flow of oil from a space in the lug nut shaft between the hole in the tank and the end of the punch body to a syringe which contains a threaded tip inserted into a threaded shaft in the fitting when suction is drawn by the syringe on the shafts after the hole is punched and the pin is backed slightly out of the hole. A threaded nut seals the threaded shaft in the fitting after the filled syringe is removed from the tool to prevent oil leakage. A first nut having a compressible, resilient O-ring partially disposed in a tapered annulus thereof is threadably advanced on the threaded body against the lug nut to prevent oil leakage from the lug nut shaft around the threaded body of the tool. A washer and second nut on the punch body combine with the first nut to form a transformer ground wire attachment assembly to ground the transformer tank through the tool and lug nut.

20 Claims, 1 Drawing Sheet

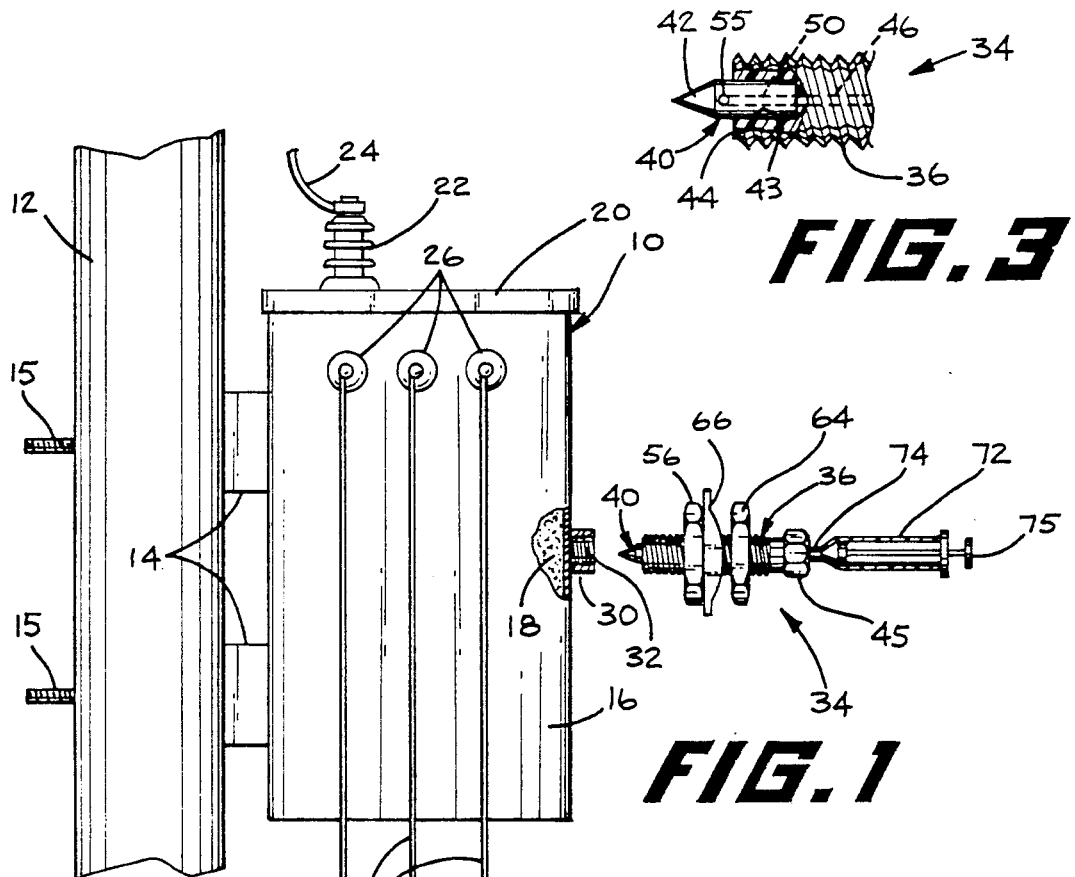
FIG. 3
FIG. 1
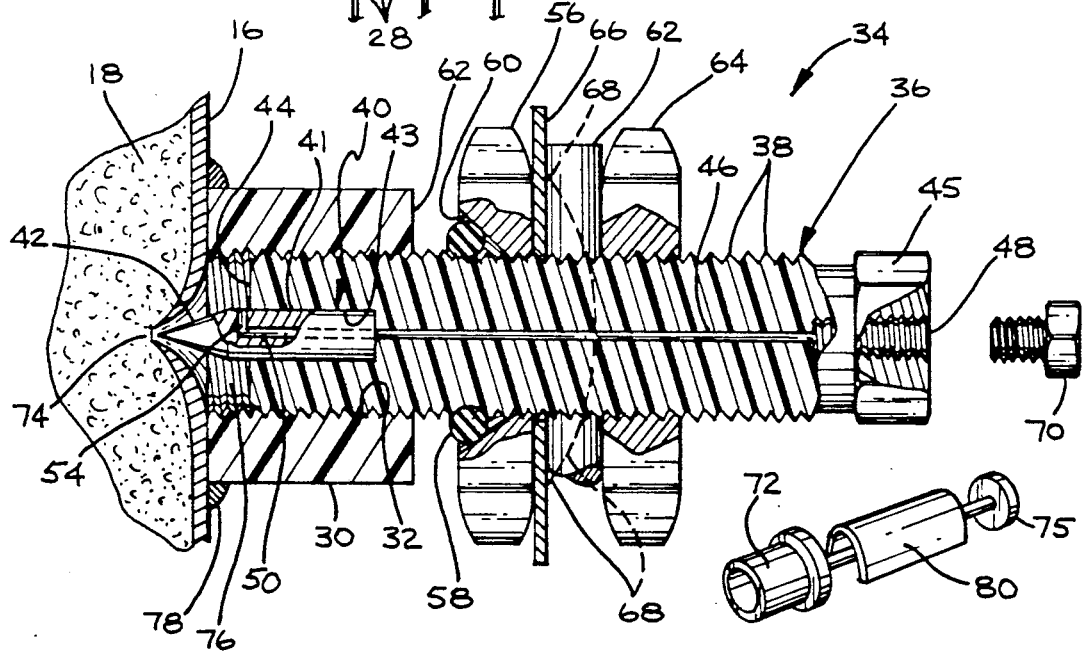
FIG. 2
FIG. 4

TOOL FOR SAMPLING OIL FROM ELECTRIC DISTRIBUTION TRANSFORMER TANKS FOR PCB CONTAMINATION

BACKGROUND OF THE INVENTION

This invention relates generally to a tool for punching a hole in the wall of an electric distribution transformer tank to remove a sample of oil therefrom without the necessity of deenergizing the transformer or removing the tank lid. More specifically, the invention relates to a transformer tank punch which is threadably insertable into an interiorly threaded hollow shaft in a conventional ground lug nut welded to the side of a transformer tank for removing a sample of oil from the tank through the tool itself by means of a suction device attached to the tool, the tool also providing a permanent seal for the hole punched in the tank and means for attaching a ground wire thereto to permanently ground the tank.

Some years ago, over a span of many years, a large number of electric distribution transformers were manufactured in this country for use by electric utilities in which the transformer coil and core were disposed in a steel tank filled with oil, which oil contained the now dreaded polychlorinated biphenyls known as PCBs. Since the devastating adverse effects of PCBs on human health have been confirmed, a nationwide cleanup effort is underway under federal government mandate.

Part of this effort involves the sampling and testing of oil contained in suspect electric distribution transformers currently in service or in place in this country which were manufactured and/or distributed during the time period when PCBs were in use in the electric utility industry. Those transformers found to contain PCB contamination in their cooling oil must be promptly removed from their location and the contaminated oil must be disposed of according to stringent EPA guidelines. The monumental task still lying ahead for the electric utility industry in this regard is staggering in its many aspects, one major aspect of which is the huge number of man hours of time that will be required for line crews to check the oil in each and every suspect transformer.

In the past, it has been necessary in many cases to de-energize each pole mounted distribution transformer to be tested so that the tank lid, upon which a high voltage primary feedthrough bushing is mounted, can be safely unbolted and removed from the top of the tank to permit access to the oil within the tank by a lineman either secured by a belt from the pole or standing in a carefully positioned bucket of a line truck. In such cases, since the lineman is operating around the primary bushing and the line leading from the bushing to the high voltage primary distribution circuit, that portion of the circuit in which the lineman might conceivably come into contact, must be de-energized before the lid can safely be unbolted and removed. Then, following sampling of the oil from the transformer tank, the lid must be secured back in place on the transformer tank and, if the oil is determined to be free of PCB contamination, the transformer must be re-energized. Otherwise, if the sample is found to be contaminated, the lid is replaced and the transformer is removed from the pole and from further service.

More recently, a gun containing a punch pin has been used to puncture a transformer tank in the air space above the oil level after which a pipette containing a manually compressible suction bulb is inserted into the puncture and down into the oil to remove an oil sample. Thereafter, the puncture is sealed using a resilient plug. Since the puncture must be made at a high level on the tank above the oil level, the worker is in dangerously close proximity to the primary circuit connected to the transformer. Moreover, the security of the resilient plug in maintaining integrity of the puncture seal over an extended period of years is questionable. Also, the violent effect of driving the puncture pin into the tank using an exploding shell exposes the worker to the possibility of contact of the pin with the energized transformer coil with the potential for disastrous results. Lastly, since some transformers under certain conditions may include a positive air pressure in the space above the oil relative to ambient, in such cases the worker could be exposed to rapid expansion of air mixed with oil expelled through the puncture which in the worst case could contain PCB and, in addition, hot or even boiling oil.

Now since many of the distribution transformers in any given electric utility service area will be free of any PCB contamination, it would be highly advantageous from the standpoint of the time required to take oil samples from these units, if the samples could be safely taken without having to unbolt and remove the tank lids and without the necessity of first de-energizing that portion of the high voltage primary circuit in which the lineman might conceivably come into contact during the lid removal activity, and without having to replace and secure the tank lid after the sample is taken and, finally, without having to re-energize the contamination free transformers after the oil samples have been obtained.

Even in the case of those transformers found to contain PCB contamination, it would be an enormous saving of time if the oil in the tank of such units could be safely sampled without the need to first de-energize the transformer, then unbolt and remove the lid to gain access to the oil, and then replace and secure the lid preparatory to bringing the transformer down off the pole. Moreover, it would also be advantageous to provide a relatively safe means for sampling oil from energized transformers by minimizing the risk of exposure to hot contaminated oil and explosion of the transformer assembly.

Generally speaking, devices for punching holes in liquid filled containers to remove some or all of the liquid have long been known in the prior art. See, for example, the tap for drawing kerosene from cans as disclosed in U. S. Pat. No. 552,408 issued to G. Barnes on Dec. 31, 1895. One disclosed example of the reference device is a handgun shaped unit having a central projecting pin surrounded by rotatable cutter elements. The pin is punched into a tin can and the device is rotated to cut a circular opening into which a threaded punch body is screwed so as to jam a rubber washer surrounding the punch body against the can wall around the hole. A screw plug is then adjusted to permit kerosene to flow from the can through the punch body and handle as desired. Obviously, the can can not be reused without the punch body being in place in the hole with the rubber washer tightly abutting the can wall around the hole to prevent leakage. This assembly, while suitable for manually punching a hole in a thin walled tin can and thereafter scribing or cutting a hole therein, is clearly unsuited for safely penetrating the heavy gauge steel wall of an electric distribution transformer tank.

Devices which permit the sampling of a fluid from within reaction vessels and other cylindrical containers with a needle syringe have also been known in the prior art. See U.S. Pat. No. 4,056,981 issued to J. Kalka et al. on Nov. 8, 1977 and U.S. Pat. No. 4,010,648 issued to R. J. Harris, Sr. et al. on Mar. 8, 1977. Both of these devices employ fittings which must be affixed to the container wall so as to communicate with the interior thereof, after which a needle syringe can be used to penetrate a seal in the fitting to access the fluid in the container. The use of such a resilient seal is not deemed satisfactory to seal a transformer tank over a term of years.

See also U.S. Pat. No. 4,809,735 issued to F. R. Volstadt et al. on Mar. 7, 1989 and U.S. Pat. No. 4,598,731 issued to D. G. Colson on July 8, 1986 which disclose two different types of screw-in-valve tapping devices for gas mains and high pressure water lines, the latter being a screw-in-type punch and the former being a screw-in-type fitting. Neither of these devices have the capability of providing a grounding assembly for attachment of a ground wire to ground a transformer tank after an oil sample has been taken. Moreover, both devices require special fittings attached to the gas or water lines before those lines are placed in use.

Lastly, see U. S. Pat. No. 3,915,192 issued to J. A. Skvarenina on Oct. 28, 1975 which discloses another type of piercing valve for connection to a puncturable conduit. The device also contains a resilient pad seal for the area being punctured to prevent leakage and a wrenchable nut on the rear end of an internally threaded cap member for permitting wrenchable rotation of the device to punch a hole in the conduit. This device also fails to provide means for attaching a transformer ground wire thereto to provide a permanent ground for a transformer tank once a liquid sample is removed therefrom. Moreover, as previously mentioned, the long term integrity of a resilient seal for a hole punched in a transformer tank is highly questionable.

By means of my invention, these and other difficulties encountered with such prior art devices are substantially overcome.

SUMMARY OF THE INVENTION

It is an object of my invention to provide a tool for piercing the metal wall of an active electric distribution transformer to obtain an oil sample from the tank without the need for de-energizing the transformer.

It is yet another object of my invention to provide a tool for facilitating the sampling of oil from an electric distribution transformer with the aid of a syringe or other suitable suction generating device removably attached to the tool.

It is yet another object of my invention to provide a tool for threadable insertion into an interiorly threaded shaft of a ground lug nut attached to the wall of an electric distribution transformer tank to punch a hole in the tank wall at the base of the lug nut shaft to obtain a sample of oil from the tank, which tool thereafter serves to permanently seal the hole to prevent oil leakage.

It is also an object of my invention to provide a tool for facilitating the sampling of oil from an electric distribution transformer tank which also permits attachment of a ground wire thereto to permanently ground the transformer tank.

Briefly, in accordance with my invention, there is provided a tool for sampling oil from an electric distribution transformer tank of the type which includes a ground lug nut containing an interiorly threaded hollow shaft rigidly attached to a wall of the tank. The tool includes a threaded body portion adapted for threadable insertion into the lug nut shaft and punch means attached to the body portion for punching a hole in the tank wall as the body portion is threadly advanced in the lug nut shaft. A wrenchable fitting for rotating the body portion to advance and retract the body portion in the lug nut shaft is also included. Shaft means defined by the punch means and body portion is also included which extends between a first opening on the punch means and a second opening on the body portion for providing an oil flow path between the openings upon application of suction to the second opening.

These and other objects, features and advantages of my invention will become apparent to those skilled in the art from the following detailed description and attached drawings upon which, by way of example, only a preferred embodiment of my invention is illustrated.

BRIEF DESCRIPTION OF THE DRAWINGS

FIG. 1 shows a side elevation view of a conventional pole mounted electric distribution transformer and a longitudinal view of a novel transformer tank punch aligned for insertion into a ground lug nut welded to the transformer tank for enabling the user to sample oil from the tank with a conventional syringe, also shown, thus illustrating one preferred embodiment of my invention.

FIG. 2 shows an enlarged longitudinal view of the tank punch of FIG. 1, the same as viewed in the latter figure, having surface portions torn away to permit viewing of the interior, the punch being threadably inserted into the transformer ground lug nut and piercing the tank wall for withdrawing an oil sample from the tank interior.

FIG. 3 shows a forward end portion of the tank punch of FIGS. 1-2 rotated 90 degrees about the longitudinal axis thereof from its position as shown in FIG. 2.

FIG. 4 shows a perspective view of a portion of the syringe of FIG. 1 with a plunger thereof in a retracted position illustrating the use of a piece of ground wire molding to lock the plunger in a retracted position when testing the ground lug nut for air leakage with suction applied.

DESCRIPTION OF THE PREFERRED EMBODIMENT

Referring now to the drawing figures, in particular FIGS. 1-3, there is shown a conventional single phase electric distribution transformer assembly 10 mounted in the usual manner on a wooden utility pole 12 as, for example, by means of brackets 14 and bolts 15. A tank 16 of the transformer assembly 10 is constructed of steel and defines an interior chamber containing the usual transformer core and windings, not shown, immersed in a pool of oil 18. The tank 16 has an open upper end covered by a removable lid or cover 20. A feed through insulator 22 is mounted on the cover 20 to which a high voltage electric distribution primary line 24 is attached. A series of feed through insulators 26 located on an upper portion of the tank 16 connect the transformer secondary windings, not shown, to a low voltage secondary customer distribution circuit 28 in the usual manner. A ground lug nut 30, exaggerated in size in FIG. 1 relative to the tank 16, is welded to the outer surface of the tank 16 and conventionally contains a hollow, interiorly threaded shaft 32 into which a bolt, not shown, can ordinarily be inserted to secure a ground wire so as to ground the tank 16 in the usual well known manner.

Now, in accordance with my invention, there is shown in a preferred embodiment thereof, a tool 34 which includes a cylindrically-shaped body portion 36 containing screw threads 38 adapted for threadable insertion into the threaded shaft 32 of the transformer ground lug nut 30. A punch means in the form of a hardened steel pin 40 is provided which contains a cylindrically shaped body section 41 and a cone shaped pin head section 42. The body section 41 is partially disposed and rigidly secured, as by press fitting, within a blind shaft 43 formed in a forward end segment of the body portion 36 such that a small portion of the section 41 projects forwardly out of the shaft 43 beyond a forward end 44 of the body portion 36. A wrenchable fitting 45 which may be in the form of a hex nut is either rigidly attached to or integrally formed on a rear end segment of the body portion 36 for permitting the tool 34 to be rotated with a wrench to advance the body portion 36 and pin 40 into the lug nut shaft 32 to punch a hole in the tank 16 and to thereafter retract the tool 34.

The body portion 36 defines an elongated hollow shaft 46 which extends along the longitudinal axis thereof from the base of the blind shaft 43 to the base of a threaded shaft 48 formed through the fitting 45 and opening onto a rear end of the latter. A forward end of the shaft 46 communicates with a hollow shaft 50 which extends along the longitudinal axis of the body section 41 of the pin 40 to a position just beyond the forward end 44 of the body portion 36. A shaft 54 extends from an opening 55 (See FIG. 3) on the surface of the body section 41 just forward of the body portion end 44 radially inwardly to intersect and communicate with a forward end of the shaft 50. The shafts 54, 50, 46 and 48 thus form an oil flow path from the opening 55 on the surface of the pin 40 to an opening of the shaft 48 on the end of the fitting 45.

The tool 34 also employs means for sealing the lug nut shaft 32 against oil leakage around and along the threads of the body portion 36 which includes a nut 56 containing a compressible, resilient O-ring 58 partially disposed in and around a tapered annulus 60. The nut 56 is threadably movable along the body portion 36 so that the O-ring 58 can be tightly compressed against an outer face 62 of the lug nut 30 around the periphery of the shaft 32 should such a seal be needed.

An optional feature of the tool 34 includes means connected to the body portion 36 for securing a ground wire 62 thereto to provide a ground for the transformer tank 16 in the form of the nut 56, a second nut 64 and a washer 66. The washer 66 contains opposite edge portions 68 which are bent at right angles to the remainder of the washer body so as to confine the wire 62 next to the body portion 36 between the washer body and the nut 64 when the nuts 56 and 64, washer 66 and ground wire 62 are tightly packed together. After a sample of oil is taken by means of the tool 34 as hereinafter explained, a cap screw 70 is threadably inserted in the threaded shaft 48 to seal the oil flow path.

Referring now also to FIG. 4, the tool 34 may be used as follows. Initially the cap screw 70 is removed from the shaft 48 and the nuts 56 and 64 and the washer 66 are loosely disposed on a rear end portion of the body portion threads 38. A workman either climbs the pole 12 or positions himself in the bucket of a line truck at a proper position within reach of the lug nut 30 but safely away from the primary bushing 22. The threads 38 of the body portion 36 are started into the threaded shaft 32 of the lug nut 30. A wrench is used on the fitting 45 to rotate the body portion 36 until the tip of the pin 40 just touches the tank 16 at the base of the lug nut shaft 32. Now the wrench is rotated a measured number of turns in the same direction just sufficiently to cause the pin 40 to pierce the tank wall 16 such that the body section 41 seals the resulting hole. The number of turns of the wrench just necessary to punch the hole with the tip of the pin 40 and thereafter seal the hole with the cylindrical body section 41 will depend upon the pitch of the threads 38, the length of the pin head 42 and the thickness of the wall 16 but should be carefully counted. The nut 56 is then immediately advanced until the O-ring 58 is mashed tightly against the face 62 of the lug nut 30.

A syringe 72 containing a tip 74 threaded in conformity with the threaded shaft 48 is threadably advanced into the fitting 45 while a plunger 75 of the syringe is fully depressed as shown in FIG. 1 until the connection between the tip 74 and fitting 45 is air tight. The plunger 75 is then retracted to determine if a vacuum can be drawn in a space 76 at the base of the lug nut shaft 32 between the tank wall 16 and the forward end 44 of the body portion 36. The purpose of this exercise is to determine if a weld 78 around and between the outside base of the lug nut 30 and the tank wall 16 is air tight. If not, as indicated by relative ease in drawing back on the plunger 75, the plunger 75 should be returned to its fully depressed condition, after which a suitable rapid drying glue should be applied over and around the weld 78 and allowed to harden to eliminate air leakage between the tank 16 and nut 30. The plunger 75 should then be drawn again, and the process repeated, as necessary, until a relatively strong vacuum can be obtained in the lug nut space 76. Once such a vacuum is obtained, a suitable spacer should be placed between a rear end of the syringe 72 and the cap on the end of the plunger 75 to hold the plunger cap in a retracted position so as to maintain the vacuum on the space 76 while the worker's hands are free. I recommend using a piece of conventional ground wire insulation molding 80 for this purpose as shown in FIG. 4 or any other suitable spacer means.

Now with the plunger 75 locked in a retracted position by the spacer 80 so as to hold a vacuum on the space 76, the worker uses one hand to torque the nut 56 and O-ring 58 tightly against the face 62 of the lug nut 30 while, at the same time, using the other hand to rotate the wrench slowly in the opposite direction about one-half turn until oil begins slowly to fill the body of the syringe 72. Upon filling of the syringe 72, the wrench is then rotated the same one-half turn in the original direction to reseat the cylindrical body section 41 back in the hole to seal the same against oil leakage, the nut 56 is given a final hand torque to assure compression of the O-ring 58 against the lug nut face 62, the filled syringe 72 is threadably removed from the fitting 45 and the cap screw 70 is tightly threaded into the threaded shaft 48 to permanently seal the same against oil leakage.

It will be recognized that it is the cylindrical body section 41 of the pin 40 which provides the permanent primary seal for the hole punched in the tank wall 16, the O-ring 58 and nut 56 providing, in combination, a secondary seal for additional security which may not be essential in all cases. In making the original measured number of rotations of the body portion 36 from the position where the pin head 42 just touches the wall 16 to the position wherein the hole is formed and the cylindrical body section 41 just seals the same, it is desirable not to make any more rotations than necessary, such that the pin head 42 does not project any further into the tank 16 than absolutely necessary. I, therefore, recommend determining how many thread pitches of the threads 38 that it will take in order to be equal to or greater than the length of the pin head up to the edge of the cylindrical body section 41 and use this number as the number of initial wrench revolutions to make the hole in the tank and seal the same, then, after confirming that a vacuum can be drawn with the syringe, back off one-half turn in the opposite direction to see if oil can be drawn from the tank. If not, then turn the wrench one-half turn in the initial direction to place the pin 40 back at its original fully advanced position and rotate the wrench an additional one-half turn in the same direction. Then back off one-half turn and observe whether this allows the syringe 72 to fill with oil. Repeat this process to advance the body portion 36 and pin 40 by a one-half turn increment followed by backing off one-half turn until the tank wall 16 is finally punched and oil flows into the syringe 72.

If the lug nut 30 is also to be used for permanently grounding the tank 16, the washer 66 should now be advanced along the body portion 36 until it is flush against the nut 56, an end portion of the ground wire 62 should be placed against the back of the washer 66, and the nut 64 should be threadably advanced until the wire 62 is tightly trapped between the washer 66 and the nut 64 with the nut 56 and O-ring 58 tight against the face 62 of the lug nut 30. The tool 34 can thus be left in this position to permanently seal the hole in the tank 16 from leakage through the lug nut shaft 32 around the body portion 36 and through the shaft 48 and to provide permanent grounding for the tank 16 when needed. Also, it will be appreciated that when used to provide grounding for the tank 16, the body portion 36, nuts 56 and 64 and washer 66 should be constructed of suitably electro-conductive metals.

Although the present invention has been described with respect to specific details of a certain preferred embodiment thereof, it is not intended that such details limit the scope and coverage of this patent other than as specifically set forth in the following claims.

I claim:

1. A tool for sampling oil from an electric distribution transformer tank of the type which includes a ground lug nut containing an interiorly threaded hollow shaft rigidly attached to a wall of said tank, said tool comprising
   a threaded body portion adapted for threadable insertion into said lug nut shaft,
   punch means attached to said body portion for punching a hole in said tank wall as said body portion is threadably advanced in said lug nut shaft,
   a wrenchable fitting for rotating said body portion to advance and retract said body portion in said lug nut shaft, and
   shaft means defined by said punch means and body portion extending between a first opening on said punch means and a second opening on said body portion for providing an oil flow path between said openings upon application of a suction through said second opening.

2. The tool of claim 1 further comprising seal means movably attached to said body portion for forming a liquid tight seal against a face of said lug nut to prevent oil leakage from the shaft of said lug nut around said body portion.

3. The tool of claim 2 wherein said seal means is threadably movable on said body portion.

4. The tool of claim 3 wherein said seal means comprises
   a first nut threadably movable on said body portion, a forward facing central surface portion of said first nut defining a tapered annulus surrounding said body portion, and
   a compressible, resilient O-ring partially disposed in and around said annulus, said O-ring being compressible between said tapered annulus and a face of said ground lug nut as said first nut is threadably advanced against the face of said lug nut for preventing oil from leaking from said lug nut shaft around said body portion.

5. The tool of claim 4 further comprising
   a second nut threadably movable on said body portion and disposed rearwardly of said first nut, and
   a washer movably mounted on said body portion between said first and second nuts, said washer containing at least one bent edge portion adapted to confine a ground wire next to said body portion between a remaining portion of said washer and one of said nuts.

6. The tool of claim 1 wherein said body portion is cylindrically shaped.

7. The tool of claim 6 wherein said wrenchable fitting is an integral part of said body portion formed on a rear end portion thereof, said second opening being located on a rear end of said fitting.

8. The tool of claim 1 wherein said punch means comprises
   a cylindrically shaped body section, and
   a cone-shaped pin head section, a first portion of said body section being rigidly held in a blind hole formed in a forward end segment of said body portion and a second portion of said body section projecting forwardly beyond a forward end of said body portion and containing said first opening.

9. The tool of claim 1 wherein said wrenchable fitting comprises a nut rigidly attached to said body portion.

10. The tool of claim 1 wherein said wrenchable fitting comprises a nut integrally formed on a rear end segment of said body portion.

11. The tool of claim 1 wherein said shaft means comprises
   a first portion of said punch means defining a first hollow shaft which extends inwardly from said first opening to a longitudinal centerline of said punch means,
   a second portion of said punch means defining a second hollow shaft which extends from an inner end of said first shaft rearwardly along the longitudinal centerline of said punch means to a rear end thereof, and
   a portion of said body portion defining a third hollow shaft which extends from a rear end of said second shaft along the longitudinal centerline of said body portion to said second opening.

12. The tool of claim 1 further comprising means for plugging said second opening to prevent oil leakage therefrom.

13. The tool of claim 12 wherein said plugging means comprises a cap screw, an end portion of said shaft means terminating at said second opening being interiorly threaded to receive said cap screw 14. The tool of claim 1 further comprising means connected to said body portion for securing a ground wire thereto to ground said transformer tank when said body portion is inserted in said lug nut.

15. The tool of claim 14 wherein said ground wire securing means comprises a pair of nuts threadably movable on said body portion, and washer means movably disposed on said body portion between said pair of nuts for confining a ground wire between said washer means and one of said nuts when said pair of nuts, washer means and ground wire are tightly packed together.

16. The tool of claim 1 wherein an end portion of said shaft means terminating at said second opening is interiorly threaded for receiving a threaded tip of a suction generating device.

17. The tool of claim 16 wherein said wrenchable fitting is integrally formed on a rear end portion of said body portion, said shaft means extending through said fitting to said second opening located on a rear end of said fitting.

18. A tool for punching a hole in a wall of an electric distribution transformer tank to facilitate the transfer of a sample of oil from said tank to a syringe attached to said tool and for thereafter providing a liquid tight seal of said hole, said tool comprising an exteriorly threaded body portion adapted for insertion into an interiorly threaded hollow shaft in a ground lug nut rigidly attached to a wall of an electric distribution transformer, punch means attached to a forward end portion of said body portion for punching the hole in said wall as said body portion is threadably advanced in said lug nut shaft, a wrenchable fitting attached to a rear end of said body portion for permitting the wrenchable rotation of said body portion to punch the hole in said wall with said punch means, shaft means formed in said punch means, body portion and wrenchable fitting extending between a first opening on said punch means and a second opening on said wrenchable fitting for providing an oil flow path between the hole, which is punched in said wall at the base of said lug nut shaft, and said second opening when a suction is applied to said shaft means by the syringe with it inserted in said second opening, means threadably movable on said body portion for forming a liquid tight seal against a face of said lug nut around said body portion when said body portion is inserted in said lug nut shaft, and means for plugging said second opening after the sample of oil has been drawn from said second opening and said syringe has been removed.

19. The tool of claim 18 further comprising means for attaching a ground wire to said tool to ground said transformer tank when said body portion is inserted in said lug nut shaft.

20. The tool of claim 18 wherein said means for plugging said second opening comprises a cap screw, an end portion of said shaft means terminating at said second opening being interiorly threaded to receive said cap screw.

* * * * *